(12) United States Patent
Hahn et al.

(10) Patent No.: US 6,545,390 B1
(45) Date of Patent: Apr. 8, 2003

(54) DEVICE FOR GENERATING HIGH-FREQUENCY MECHANICAL VIBRATIONS FOR A DENTAL HANDPIECE

(75) Inventors: Rainer Hahn, Tübingen; Uwe Grotz, Löchgau, both of (DE)

(73) Assignee: Durr Dental GmbH & Co. KG (DE)

( * ) Notice: Subject to any disclaimer, the term of this patent is extended or adjusted under 35 U.S.C. 154(b) by 0 days.

(21) Appl. No.: 09/547,151

(22) Filed: Apr. 11, 2000

(30) Foreign Application Priority Data

Apr. 11, 1999 (DE) .......................................... 199 16 161

(51) Int. Cl.[7] .................................................. H02N 2/06
(52) U.S. Cl. .................................. 310/317; 310/316.01
(58) Field of Search .............................. 310/316.01, 317

(56) References Cited

U.S. PATENT DOCUMENTS

| | | | | |
|---|---|---|---|---|
| 4,012,647 A | * | 3/1977 | Balamuth et al. ...... | 310/316.01 |
| 4,256,987 A | * | 3/1981 | Takeuchi et al. ....... | 310/316.01 |
| 4,403,176 A | * | 9/1983 | Cranston ................... | 318/114 |
| 4,965,532 A | * | 10/1990 | Sakurai .................. | 310/316.01 |
| 5,113,116 A | * | 5/1992 | Wilson .................... | 310/316.01 |
| 5,477,099 A | * | 12/1995 | Suganuma ............. | 310/316.01 |
| 5,900,690 A | * | 5/1999 | Gipson et al. ......... | 310/316.01 |
| 5,931,836 A | * | 8/1999 | Hatta et al. ................... | 606/38 |

FOREIGN PATENT DOCUMENTS

DE 27 10 049 A1 8/1977 ............ A61C/1/07

* cited by examiner

*Primary Examiner*—Thomas M Dougherty

(57) ABSTRACT

A device for generating high-frequency mechanical vibrations for dental purposes comprises a current detector (50) fitted in the supply line of a vibration generator (12). The output signal of the current detector (50) is transmitted to one of the inputs of a control circuit (74), which at its other input receives a supply current nominal value signal. The output of the control circuit (74) is connected to the control terminal of a controllable oscillator (42), which together with a power stage (46 to 48) prepares the supply current for the vibration generator (12). In this manner, a constant output amplitude of the vibration generator is obtained independent of the load coupled to said vibration generator at any given time.

11 Claims, 4 Drawing Sheets

Figure 1:
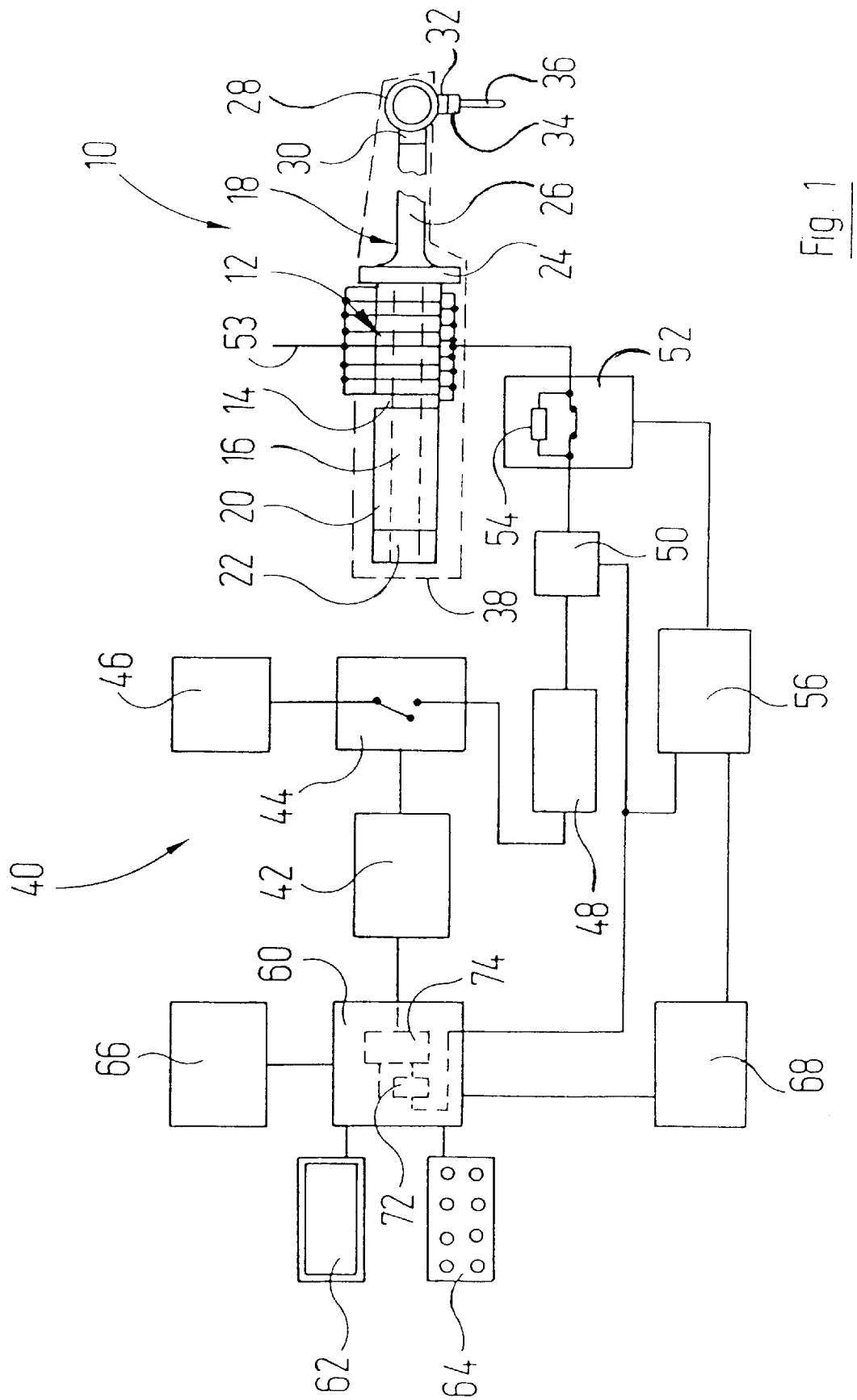

DEVICE FOR GENERATING HIGH-FREQUENCY MECHANICAL VIBRATIONS FOR A DENTAL HANDPIECE

The invention relates to a dental device for generating preferably high-frequency mechanical vibrations for a dental handpiece according to the preamble of claim 1.

The term high-frequency within the context of the present description and the claims is understood to be a frequency lying in the ultrasonic range. However, the invention can also be used in the audible frequency range and in the infrasonic range.

When using dental handpieces, which comprise a tool driven at high mechanical frequency, the loading of the device generating the high-frequency mechanical vibrations is closely dependent upon the damping of the tool by the respective tissue which is treated. This loading is dependent upon the complex contact geometry between tool and tissue surface as well as the pressure with which the dentist presses the tool against the tissue which is to be treated. If the handpiece operates with a coupling fluid acting between the tool and the tissue surface, then the loading of the device for generating vibrations is also dependent upon whether, and how much coupling fluid is supplied.

In order to guarantee a level of efficiency of the ultrasonic handpiece which can be used in practice, it is necessary for the dentist to vary the contact pressure of the tool (and therefore of the handpiece). Finally, only very imprecise tactile feedback is available to the dentist during this process, since the high frequencies, at which the tool is mechanically vibrated, cannot be perceived by the human ear or cannot be perceived with the desired precision.

Furthermore, the dentist cannot respond so quickly to rapid load changes in order to reliably rule out the occurrence of excessively high vibrations resulting in damage to the handpiece or tool, or there is danger of a decrease or cessation in the vibration going unnoticed by the dentist, so that the treatment effect is reduced or ceases altogether.

It is therefore the object of the present invention to develop a device for generating high-frequency mechanical vibrations for a dental handpiece in such a manner that a reliable automatic limiting of the vibration amplitude is ensured.

This object is attained according to the invention by a device having the features disclosed in claim 1.

Advantageous developments of the invention are disclosed in the subclaims.

In the vibration generating devices used in the field of dentistry, which usually operate in the ultrasonic range, it has been found that the supply current supplied to the actual vibration generator (usually a stack of piezoelectric disks) is a good measure of the instantaneous amplitude of the vibration generated. In the device according to the invention as disclosed in claim 2, this supply current is used as an actual value for an amplitude control, which not only prevents unduly high amplitudes, but also ensures a constant amplitude of the vibration generator and therefore also of the tool during operation under varying loading.

According to claim 3, a precise control of the amplitude is obtained by slight variations in the frequency of the oscillator. A steep control characteristic curve is therefore obtained. The development of the invention according to claim 4 also allows for the amplitude control in a particularly simple manner via a control signal, by means of which the control terminal of a controllable oscillator can be actuated. In this manner of proceeding, use is made of the fact that each frequency variation results in an amplitude variation on a flank of the resonance curve of the overall system, which is formed by the operating circuit, the vibration generator, the tool and the load, or more precisely, a frequency change in the direction of the maximum of the resonance curve results in an increase in amplitude, whilst a frequency change in the other direction results in an amplitude reduction. Controllable oscillators can also be obtained as economic and reliable components.

The development of the invention according to claim 4 is advantageous with a view towards a rapid adjustment of the actual amplitude to the nominal amplitude. In this manner, excessive mechanical loading of the parts of the device lying between the vibration generator and the tool, which could result in material failure, can be avoided.

The rapid limiting of the supply current supplied to the vibration generator can be realised in a particularly simple manner according to claim 5 in that the current limitation or a current interruption is effected directly upstream of the vibration generator, so that inertia of electronic logic circuits and power stages does not play a role.

The manner of realising the current limitation disclosed in claim 6 allows for a low level of loss during correct operation of the device.

The development of the invention according to claim 7 also promotes the immediate reduction of excessive supply current for the vibration generator. The variant according to claim 7 offers the advantage that the current limitation is effected via the control signal for the oscillator in a manner requiring a low level of power, so that it is not necessary to provide a current limiting circuit designed for higher currents.

Since, according to the invention, it is possible to avoid mechanical overloading of the vibration generator and the parts driven thereby even during varying load conditions, it is also possible to select a higher mean amplitude used for operating (not requiring any safety margin accounting for varying load conditions). However, this then results in higher mean load values. In the case of a vibration generator which comprises a plurality of piezoelectric disks resting against one another in a prestressed manner, it is therefore also of particular interest to also ensure reliable and safe contacting of the individual piezoelectric disks over long-term operation and also to prevent fatigue failure in the power connections to the piezoelectric disks. To this end, it is proposed in claim 8 to apply the electrode layers of the various disks directly onto the disks (by electroplating, evaporation, sputtering, etc.) instead of placing them as separate elements between the disks, as in conventional fashion.

In this respect, it is then particularly advantageous according to claim 8 if the various electrode layers each comprise a connecting section constructed on the cylindrical surface of the disks. In this manner, the connecting sections are particularly reliably protected against deformation and fatigue failure.

With the development of the invention according to claim 9, a symmetrical application of potential to the electrode layers is ensured.

In a device according to claim 10, the equivalent electrode layers of the various disks can be connected in a simple manner by axial electrical conductors, which are soldered onto the outside of the disk stack.

With the development of the invention according to claim 11, a voltage arc-over is reliably prevented between the electrode layers lying at different potential and connecting conductors, which are connected to the connecting sections.

Figure 2:
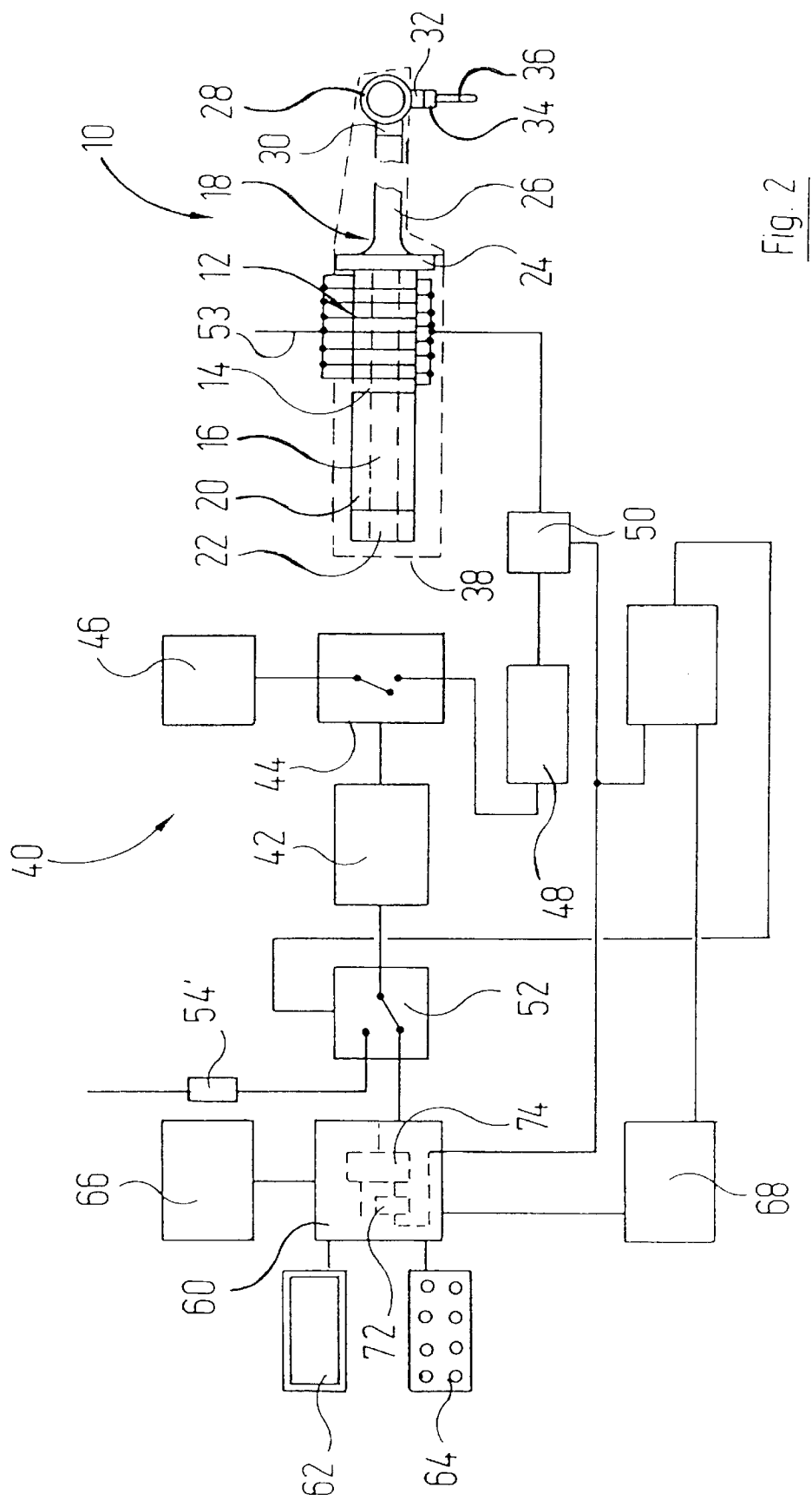
Figure 3:
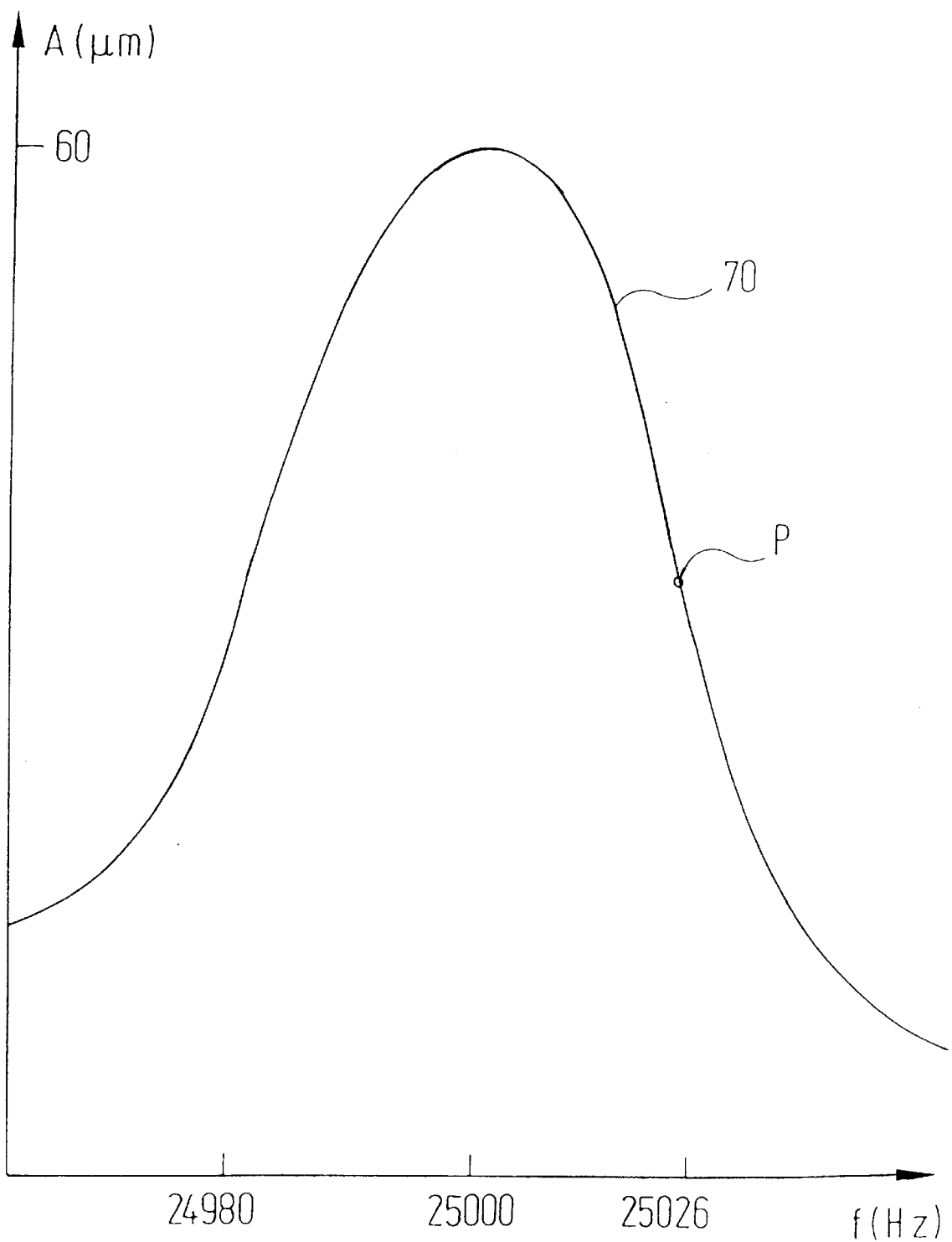
Figure 4:
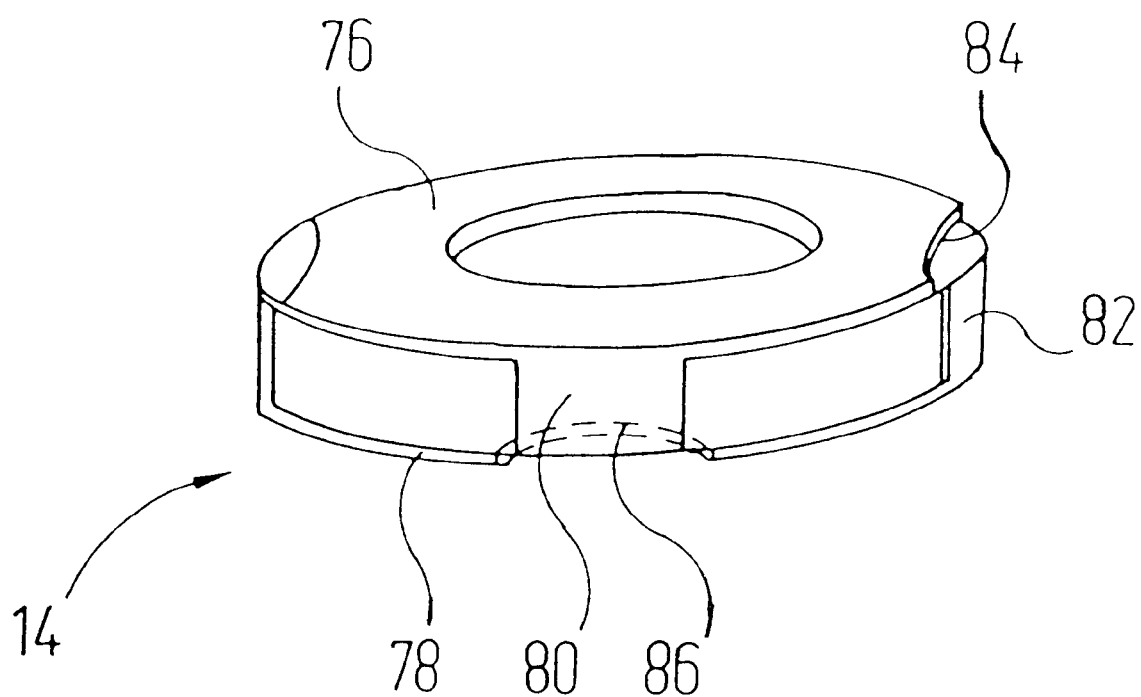

The invention will be explained in further detail in the following with the aid of embodiments with reference to the drawings. In the drawings:

FIG. 1: is a schematic view of the electro-mechanical parts of a dental ultrasonic handpiece and an operating circuit for said handpiece;

FIG. 2: is a similar view to FIG. 1, in which a modified operating circuit is shown;

FIG. 3: is a graph showing the resonance curve of the overall vibratory system, which is formed by the ultrasonic handpiece and its operating circuit; and FIG. 4: is a perspective view of a piezoelectric disk and electrode layers supported by said disk.

A dental ultrasonic handpiece is designated in its entirety in FIG. 1 by the reference 10.

It comprises a stack 12 of piezoelectric disks 14, which are fitted with prestressing onto a rear shaft section 16 of a sonotrode designated in its entirety by the reference 18. Also fitted on the shaft section 16 is a counterweight 20, and the disk stack 12 and the counterweight 20 are clamped against a flange section 24 of the sonotrode 18 by threaded ring 22.

The sonotrode 18 also comprises a drive section 26, which lies in front of the flange section 24 and onto whose free end a deflection ring 28 is fitted. The latter is constructed in such a manner that vibration antinodes are simultaneously obtained at a first connecting section 30, which is supported by said deflection ring 28 and is connected to the sonotrode 18, and at a second connecting section 32 offset through 90° relative to the first connecting section 30. The connecting section 32 supports a collet 34, in which a rod-shaped ultrasonic tool 36 is fitted.

The entire arrangement is integrated into a housing 38 indicated by broken lines.

In order to generate an operating current for the disk stack 12 (or a different vibration generator providing high-frequency mechanical vibrations, e.g. a magnetostrictive element) and for maintaining constant amplitudes of the sonotrode 18 independent of the load ratios at the tool 36, an operating circuit is provided, which is designated in its entirety by the reference 40. The operating circuit 40 comprises a voltage-controlled oscillator (VCO) 42. The output signal of said oscillator 42 is used for actuating a rapid semi-conductor switch 44, which can be a power transistor, for example, such as a MOSFET. The rapid semi-conductor switch 44 chops the direct voltage transmitted by a direct voltage source 46 at a frequency corresponding to the ultrasonic range (e.g. approximately 25 kHz). The direct voltage, which is square-wave modulated in this manner and whose amplitude can typically lie between 20 and 40 V, is supplied to an amplitude converter 48. This is typically a transformer with a suitable transformation ratio (in practice, factor 2 to 4).

The current transmitted by the amplitude converter 48 is measured by a current detector 50. The current detector 50 has a short time constant, which corresponds to or is less than the reciprocal of the operating frequency of the controllable oscillator 42. In this manner, the actual value of the supply current for the piezoelectric disk stack 12 can be measured with high time resolution. The current flowing from the current detector 50 to the disk stack 12 runs through a controllable switch 52, which also comprises a short response time comparable to or less than the reciprocal of the frequency of the oscillator 42, to the disk stack 12 and from here returns via an earth line 53.

The controllable switch 52 is normally closed and is bridged by a resistance 54, which limits the supply current to a value at which unduly high mechanical loading, which could result in fatigue failure, occurs neither at the disk stack 12, nor at the sonotrode 18, nor at the deflection ring 28, nor at the tool 36.

It is also possible, if desired, to omit the resistance 54, so that the supply current is completely interrupted under emergency conditions, which will be described below.

The actuation of the controllable switch 52 is effected by the output signal of a comparator 56, which at one input receives the output signal of the current detector 50 of low time constant and at the other input receives a nominal value signal determining the maximum permissible current to the disk stack 12. The comparator 56 is also rapid, i.e. it has a time constant which corresponds to or is less than the reciprocal of the frequency of the oscillator 42.

In the manner described above, it is ensured in the event of an abrupt load reduction that the supply current to the disk stack 12 is returned to a non-damaging value within a short time interval which corresponds to a fraction of a vibration amplitude or a few vibration amplitudes.

For the overall control of the ultrasonic handpiece 10, a processor 60 is provided. This cooperates with a display 62, which can be a small LCD screen, for example. Current operating data can be entered into the processor 60 via an input panel 64, e.g. the nature of the tool 36 which is being used, the nature of the work carried out (polishing of a tooth surface, abrasive removal of plaque, drilling of cavities). The processor 60 cooperates with a mass store 66, e.g. a ROM, in which the program according to which the processor 60 operates is stored together with characteristic data for different tools and different procedures which are to be carried out.

From the data stored in the mass store 66 and the input at the input panel 64, the processor determines nominal values for the desired operating amplitudes of the sonotrode 18 (and therefore of the tool 30) and a nominal value for the supply current, which must not be exceeded during operation. This signal is transmitted via a D/A converter 68 as a reference signal to the second input of the rapid comparator 56.

The processor 60 also generates the control signal for the voltage-controlled oscillator 42.

The ultrasonic handpiece described above with its associated operating circuit operates as follows:

After entering the data for the tool 36 and the procedure which is to be carried out at the input panel 64, the processor determines, by taking into account data stored in the mass store 66, a normal operating frequency for the oscillator 42. This is selected in such a manner that an operating point (cf. FIG. 3) of the overall vibratory system, which is formed by the operating circuit 40, the disk stack 12, the sonotrode 18, the deflection ring 28 and the tool 36, lies on the high-frequency flank of the resonance curve of the overall system, which is shown in FIG. 3 at 70. It can be seen that by lowering the oscillator frequency, the amplitude is increased, starting from the basic operating point P, whilst a frequency increase results in a reduction in the amplitude.

In a practical embodiment, the maximum of the resonance curve can lie at approximately 25,000 Hz and the half width of the resonance curve can lie between 20 and 100 Hz depending on the class of the overall vibratory system. The maximum amplitude obtained at resonance can lie between 50 and 100 $\mu$m. Typical operating amplitudes, which can be increased without delay, lie between 30 and 80 $\mu$m.

At a further input, the processor 60 now receives the output signal of the current detector 50. This signal is transmitted via an A/D converter 72 contained within the processor 60 to one input of a software control circuit 74, whose other input receives a nominal current signal, which the processor 60 has derived from the characteristic data for the respective procedure which is to be carried out and from the tool characteristic data.

The output signal of the control circuit 74 represents (optionally following conversion into an analogue signal) the control signal for the oscillator 42.

If the tool 36 is not coupled to tissue which is to be treated, then as a result of the lack of damping by a load the amplitude of the sonotrode 18 increases, which can be registered by a corresponding increase in the supply current flowing through the disk stack 12. The control circuit 74 now changes the control signal for the oscillator 42 in the form of a frequency increase, so that the vibration amplitude is reduced according to the resonance curve 70 of FIG. 3.

If the tool 36 is loaded by coming into contact with a tissue which is to be treated, e.g. a tooth coating, then the amplitude of the sonotrode 18 and therefore also the current flowing through the disk stack 12 falls. The control circuit 70 recognises this and now changes the control signal for the oscillator 42 in the form of a reduction in the oscillator frequency. Consequently, the amplitude of the sonotrode 18 is increased again, until the desired amplitude nominal value is reached.

If there is a vary rapid load change for the sonotrode 18, e.g. as a result of breakage of the tool 36 or another rapid variation in the acoustic resistance, then the comparator 56 recognises this and opens immediately (within a fraction of a cycle or a few cycles of the controllable switch 52). From this moment in time, the disk stack 12 is then only acted upon by the reduced supply current determined by the resistance 54 or is even no longer acted upon by supply current. As a result of this rapid reduction in the supply current, mechanical damage to the ultrasonic handpiece by very rapid load changes is prevented.

In the modified embodiment according to FIG. 2, the controllable switch 52 is not fitted in the supply line to the disk stack 12, but in the control line leading to the controllable oscillator 42, and is constructed as a reversing switch. Instead of the variable control signal prepared at the output of the processor 60, upon-actuation the reversing switch 52 transmits a fixed control signal (indicated by a resistance 54') to the oscillator 42, which is selected in such a manner that the amplitude remains within the permissible range even when the load is zero.

In this manner, the control signal for the controllable oscillator 42 is limited, and in analogous fashion a rapid limiting of the supply current is obtained in the event of a rapid load change.

FIG. 4 is a perspective view of a piezoelectric disk 14. On its upper side, the annular disk 14 supports an electrode layer 76, on its underside an electrode layer 78.

The electrode layer 76 has two connecting sections 80, which are offset through 180° in the circumferential direction and extend over part of the circumferential surface of the disc. In corresponding fashion, the lower electrode layer 78 supports two connecting sections 82, which are arranged opposite one another and also lie on the circumferential surface of the disk 12. The connecting sections 80 and 82 are offset relative to one another through 90°.

In the region of the connecting sections of the respective other electrode layer, the electrode layers 76, 78 are provided with circular arc-shaped peripheral recesses 84, 86, so that the connecting sections of equivalent electrode layers can be connected to one another by conductors directly soldered in place, without the danger of a short-circuit.

The electrode layers 76, 78 and the connecting sections 80, 82 are fitted in situ onto the disks 12, e.g. deposited by evaporation, sputtering or electroplating. They can also be produced by screen printing or another suitable method.

What is claimed is:

1. A dental device for generating high-frequency mechanical vibrations for a dental handpiece, comprising
    a vibration generator,
    a controllable oscillator,
    a power stage connected downstream of said oscillator, and
    a control circuit,
    wherein limiting means are provided that limit a supply current supplied to the vibration generator below a predetermined maximum value,
    and wherein the limiting means comprise a current detector that is fitted between the power stage and the vibration generator and whose output signal is supplied to one input of the control circuit that receives a current nominal value signal at a second input and whose output is connected to a control terminal of the controllable oscillator.

2. A device as claimed in claim 1, wherein the vibration generator comprises a plurality of piezoelectric disks, which rest against one another with prestressing and on their end faxes support electrode layers, which are produced in situ.

3. A device as claimed in claim 1, wherein the current nominal value signal is selected in such a manner that the operating point of the overall vibratory system formed by the vibration generator and load coupled therewith lies on a flank of the resonance curve of the overall vibratory system, preferably on a high-frequency flank of the resonance curve.

4. A device as claimed in claim 1, wherein the current detector ha a time constant which is comparable with or shorter than the cycle of the oscillator.

5. A device as claimed in claim 1, wherein a current limiting circuit is fitted in the line leading from the power stage to the vibration generator.

6. A device as claimed in claim 5, wherein the current limiting circuit comprises a normally closed switch, which is actuated by the output signal of a comparator, which is acted upon by the output signal of the current detector fitted between the output of the power stage and the vibration generator and by a maximum current signal, the current detector and the comparator having time constants comparable with or less than the cycle of the oscillator.

7. A device as claimed in claim 1, wherein the control terminal of the controllable oscillator can be acted upon via a switch by a fixed control signal, which is acted upon by the output signal of the current detector fitted between the output of the power stage and the vibration generator and by a maximum current signal, the current detector and the comparator having time constants comparable with or less than the cycle of the oscillator.

8. A device as claimed in claim 2, wherein the electrode layers each comprise a moulded-on connecting section, which extends over a section of the circumferential surface of the disk.

9. A device as claimed in claim 8, wherein the electrode layers each comprise tow connecting sections lying opposite one another.

10. A device as claimed in claim 2, wherein the connecting sections, which are connected to the electrode layer of one or the other end face of the disk, are offset relative to one another in the angular direction.

11. A device as claimed in claim 8, wherein the electrode layers and the connecting sections of the respective opposing electrode layer comprise adjacent peripheral recesses.

\* \* \* \* \*